US012797156B2

(12) United States Patent
Holthaus

(10) Patent No.: US 12,797,156 B2
(45) Date of Patent: Nov. 17, 2026

(54) MEDICAL MULTI-DYE FLUORESCENCE IMAGING SYSTEM AND METHOD

(71) Applicant: OLYMPUS Winter & Ibe GmbH, Hamburg (DE)

(72) Inventor: Carsten Holthaus, Barsbuettel (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 271 days.

(21) Appl. No.: 18/511,209

(22) Filed: Nov. 16, 2023

(65) Prior Publication Data

US 2024/0268647 A1 Aug. 15, 2024

Related U.S. Application Data

(60) Provisional application No. 63/444,624, filed on Feb. 10, 2023.

(51) Int. Cl.

| | |
|---|---|
| ***A61B 90/00*** | (2016.01) |
| ***A61B 1/00*** | (2006.01) |
| ***A61B 1/04*** | (2006.01) |
| ***A61B 1/06*** | (2006.01) |

(52) U.S. Cl.

CPC .......... *A61B 90/36* (2016.02); *A61B 1/00186* (2013.01); *A61B 1/043* (2013.01); *A61B 1/0638* (2013.01); *A61B 1/0646* (2013.01); *A61B 2576/00* (2013.01)

(58) Field of Classification Search

CPC ..... A61B 90/36; A61B 1/00186; A61B 1/043; A61B 1/0638; A61B 1/0646; A61B 2576/00

See application file for complete search history.

(56) References Cited

U.S. PATENT DOCUMENTS

2004/0186351 A1* 9/2004 Imaizumi ............. A61B 1/0646 600/476
2005/0113641 A1* 5/2005 Bala ..................... A61B 1/0646 600/104
2005/0182321 A1* 8/2005 Frangioni ............ A61B 5/0071 600/431
2011/0082369 A1* 4/2011 Mohr ..................... A61B 1/043 600/431

(Continued)

FOREIGN PATENT DOCUMENTS

DE 11 2017 004 154 T5 5/2019
DE 10 2020 117 579 A1 1/2022
DE 10 2020 123 365 A1 3/2022

*Primary Examiner* — Sean D Mattson
(74) *Attorney, Agent, or Firm* — Scully, Scott, Murphy & Presser, P.C.

(57) ABSTRACT

A medical multi-dye fluorescence imaging system and method. In a first lighting mode for a first predetermined dye fluorescing in the visible spectrum, a first narrow band fluorescence excitation light is generated in the visible spectrum and a second narrow band fluorescence excitation light is generated in the far red or near infrared spectrum, fluorescent image data are taken with a first image sensor sensitive in the visible spectrum and background image data are taken with a second image sensor sensitive in the far red or near infrared spectrum, wherein the visible spectrum fluorescent image data are overlaid over the far red or near infrared background image data.

22 Claims, 2 Drawing Sheets

(56) References Cited

U.S. PATENT DOCUMENTS

| | | | | |
|---|---|---|---|---|
| 2015/0381909 | A1 * | 12/2015 | Butte | A61B 1/00188 250/578.1 |
| 2019/0170647 | A1 * | 6/2019 | Ikenaga | A61B 1/0638 |
| 2022/0007942 | A1 * | 1/2022 | Stith | A61B 1/043 |

* cited by examiner

MEDICAL MULTI-DYE FLUORESCENCE IMAGING SYSTEM AND METHOD

CROSS-REFERENCE TO RELATED APPLICATION

The present application is based upon and claims the benefit of priority from U.S. Provisional Application No. 63/444,624 filed on Feb. 10, 2023, the entire contents of which is incorporated herein by reference.

BACKGROUND

Field

The present disclosure relates to a medical multi-dye fluorescence imaging system and method.

Prior Art

A medical application of fluorescence imaging, a subtype of molecular imaging, is fluorescent image-guided surgery, a medical imaging technique used to detect fluorescent substances during surgery with the purpose of guiding the surgical procedure and providing the surgeon with real time visualization of the operating field, both in open surgery and in endoscopic procedures. Fluorescence dyes (fluorophores) commonly used in fluorescent image-guided surgery for different applications include indocyanine green (ICG) and others in the optical and near infrared spectrum.

One or more light sources are used to excite and illuminate the sample containing the chosen fluorescent dye. Light is collected using optical filters that match the emission spectrum of the chosen fluorescent dye. Imaging lenses and digital cameras (CCD or CMOS) are used to produce the final images.

In fluorescence imaging guided surgery, the surgeon gets to view a composite image with an overlay of the fluorescent image over a non-fluorescent background image for easy localization of the fluorescent areas within its surroundings. There are different ways to achieve such an overlay image. One option is that the background image and the overlay image are recorded simultaneously with different video chips and the recorded images are then electronically merged. In this case, the additional chip for the fluorescence is usually sensitive in a wavelength range outside the visible spectrum at wavelengths>700 nm.

Another option is to record a white light image and a fluorescent image alternating with the same video chip by also changing the illumination between white light and excitation light.

If the images may be recorded simultaneously and a camera head with three CCD or CMOS video chips for the blue, green and red channels are used also the blue and green video chips can be used for the white light image and the red video chip can be used for the fluorescent image in the near infrared.

One type of medical imaging system comprises a camera head with exchangeable optical units that are designed for endoscopic or open surgery applications. A camera head usually comprises one or more optical sensors as well as a cone adapter connecting and securing the ocular cones of optical imaging units to the camera head. Such optical imaging units may be devices for endoscopic procedures, such as rigid telescope type endoscopes having an optical assembly at their distal tip for forming an image of the specified field of view, and one or more relay lens units for relaying the image to the endoscope's ocular for view with the unaided eye, or alternatively, the camera head. For this purpose, the camera head comprises imaging optics that focus on the location of the virtual image projected by the ocular lens of the attached telescopes at their own focal distance. This focal distance is standardized between different types of telescopes, since they have to be usable with the unaided eye.

For the purpose of capturing the operating area in open surgery, the optical imaging units are often designed to create a virtual image of the operating area with a predefined field of view at a predefined working distance. A typical example is the so-called exoscope, which resembles a short endoscope with an objective lens, a set of relay lens units and an eyepiece. The optical properties of the objective lens are quite different from those of objective lenses of endoscopes because of their very different focal lengths, since, unlike an endoscope, an exoscope is designed to operate outside a human body instead of inside the human body.

Since the camera head has its own imaging optics, an attachment lens system, also called a head lens, may be attached to the camera head's cone adapter that provides the combined optical system of the attachment lens system and the camera head's optical imaging system with the focal length and other optical properties necessary for viewing and recording the operating area.

In order to illuminate the operating area, the medical imaging systems usually comprise an illumination light generating unit comprising one or more light sources generating the illumination light. The illumination light is transported from the illumination light generating unit to the distal end of an optical imaging unit through a fiber bundle, where it exits the fiber bundle. Although they may have light shaping units such as lenses, endoscopes and exoscopes usually do not comprise any light shaping units at the tip, so that the irradiance distribution at the field of operation is mainly defined by the irradiance distribution with which the light enters the fiber bundle from the light source.

Modern medical imaging systems implement the above-described versatility of endoscopic or open surgery imaging with various telescopes and exoscopes for different applications that can be attached to the system's camera head, which is controlled by a central controller (CCU) or controller. The telescopes and exoscopes may have an illumination light connector to be connected to an illumination light generating unit of the medical imaging system via light fibers. Such systems may furthermore implement fluorescence imaging for fluorescence imaging guided surgery.

Fluorescence imaging is a form of molecular imaging, which generally encompasses imaging methods for visualizing and/or tracking of molecules having specific properties that are used for molecular imaging. Such molecules can be substances that are endogenous to the body, or dyes or contrast agents that are injected into the patient. MRI and CT, for example, therefore, also fall under the term "molecular imaging". Fluorescence imaging as a variant of molecular imaging uses the property of certain molecules (fluorophores), which emit light of certain wavelengths when excited by or having absorbed light of certain wavelengths.

For the purpose of fluorescence imaging, the system's camera head includes sensors that are sensitive in the visible spectrum and in the near infrared spectrum, while the system's illumination light generating unit has a light source for white light to illuminate the operating area with white light as well as at least one excitation light source designed to illuminate the operating area with light that includes an excitation wavelength capable of exciting a fluorescent substance or dye that has been injected into the operating area, to return fluorescence emission. In order to produce a sufficient fluorescence response from the fluorescent dye to produce a usable fluorescent image, the intensity of the fluorescence excitation light needs to be high. The excitation light source may comprise a laser, a light emitting diode or a Xenon lamp with appropriate filters, the wavelength depending on the dye used. For indocyanine green (ICG), e.g., which emits fluorescence light between 750 nm and 950 nm, an excitation wavelength may be between 600 nm and 800 nm. After being excited, the dyes shed the excitation energy by emitting light at slightly longer wavelengths than that of the excitation light. Other wavelengths may be used as excitation wavelengths depending on the type of dye used. This can include wavelengths that are further inside the visible spectrum.

Since the fluorescence light is typically much weaker than the white light reflected from the tissue that is being operated on, it is necessary to provide apparatus and methods to enhance, separate or isolate the fluorescence light signal from the white light signal, as well as to prevent the fluorescence light signal from being drowned out by the excitation light.

In some medical imaging systems, for example, this may be done by time multiplexing, i.e., the alternating of white light and excitation light illumination. While this method provides a good separation, it may be found irritating by sensitive personnel due to a high speed flicker of the illumination light, especially in open surgery, where the personnel present is exposed to the changing lighting, or due to a slow repetition rate of the images produced therewith.

When using fluorescent dyes whose excitation and fluorescence spectrum is in the visible light, the excitation light necessarily lies within the same visible spectrum as white illumination light used for background images. Since the fluorescence light is much weaker than the white illumination light reflected from the tissue under observation, there is no feasible way to obtain usable fluorescent imagery when using visible spectrum excitation light and white illumination light simultaneously.

SUMMARY

An object is to provide improved apparatus and methods for multi-dye fluorescence imaging in the case that at least one of the fluorescence dyes is excited in the visible spectrum.

Such object can be solved by a medical multi-dye fluorescence imaging system comprising a controller comprising hardware, several light sources controlled by the controller, at least one imaging unit comprising a first image sensor sensitive in the visible light spectrum and a second image sensor sensitive in the far red and/or near infrared light spectrum, an image processor comprising hardware and controlled by the controller, the image processor being configured to receive image data from the first image sensor and from the second image sensor and to combine the image data into composite images in which fluorescent images are overlayed over background images, wherein the controller being configured to control the light sources and the image processor according to a first lighting mode for at least one first predetermined fluorescent dye fluorescing in the visible light spectrum, the first lighting mode comprising activating a first light source of the several light sources configured to produce excitation light for the at least one first predetermined dye in the visible light spectrum, activate a second light source of the several light sources configured to produce light in the far red and/or near infrared light spectrum, and control the image processor to overlay image data from the first image sensor over image data from the second image sensor.

With its first lighting mode, the system can provide the capability of doing fluorescent imagery in the visible spectrum that can be overlaid over a background image. The background image can be done with light in the far red or near infrared spectrum. In this case, the background image lacks the full color definition of white illumination lighting and can, for example, be displayed as monochromatic image. For the purposes of fluorescent image-guided surgery, the visual information provided by a monochromatic background image overlaid with an image of fluorescence imaging can usually be sufficient for the surgeon. In contrast to using a white light background image, this lighting mode does not suffer from the stroboscopic effect and lower frame rates that otherwise result when switching from visible spectrum excitation lighting to white illumination lighting and back between subsequent images.

Within the system, the image processor can be a sub-unit of the controller or separate from the controller. The fluorescence excitation light sources may, e.g., be laser sources, narrow-band and high intensity LED sources or Xenon lamps with corresponding filters that let pass through the needed fluorescence excitation wavelengths.

Within the context of the present application, the terms visible spectrum, far red spectrum and near infrared spectrum are used according to their common definitions. They are to be viewed within the context of fluorescence imaging, where some dyes may have an excitation spectrum in the visible spectrum and others may be excited in the near infrared. Furthermore, the far red part of the spectrum is still within the visible spectrum, which ranges from violet and blue on the short wavelength side to the far red range, which itself borders the near infrared range, approximately at 800 nm and longer.

The sensitivity of an image sensor usually drops off more or less steeply at the edges of its sensitivity. In the context of the present application, the sensitivities of the sensors used within the system can overlap slightly, but the need not necessarily overlap. For example, an image sensor sensitive in the far red and/or near infrared spectrum may or may not have some overlap in sensitivity with an image sensor that can be sensitive in the visible spectrum.

In embodiments, the controller can be additionally configured to control the light sources and the image processor according to a second lighting mode for at least one second predetermined fluorescent dye fluorescing in the far red and/or near infrared light spectrum, the second lighting mode comprising activating a third light source of the several light sources configured to produce excitation light for the at least one second predetermined dye in the far red and/or near infrared light spectrum, activate a fourth light source of the several light sources configured to produce white illumination light, and control the image processor to overlay image data from the second image sensor over image data from the first image sensor. This second lighting mode provides the circumstances for the reverse case where the background image can be a full-color image provided with white illumination and the fluorescent image can be done in the far red or infrared spectrum.

In embodiments, the at least one imaging unit can comprise at least one of at least one first filter configured and located to prevent excitation light from the first light source from reaching the first image sensor and at least one second filter configured and located to prevent excitation light from the third light source from reaching the second image sensor. These filters can be configured to protect the image sensors from being overwhelmed by fluorescence excitation light generated by the first and third light sources in the visible and far red/near infrared spectra, respectively, and reflected back to the image sensors. They can be configured to cut out a narrow band of the wavelength spectrum around the respective excitation wavelength. In the case of a laser light source, the filter band can have a width of several nm, in the case of a strong LED light source the filter band can be a few nm wider than the LED light bandwidth. Each filter can have one or more filter bands for one or more light sources and excitation wavelengths.

According to an embodiment, the second light source can be configured to emit light in a spectrum lying at least partially outside of any frequencies filtered out by the at least one second filter. According to this embodiment, there can be one or more fluorescence excitation light sources in the far red and/or near infrared light spectrum for one or more dyes that fluoresce in the far red and/or infrared spectrum and the second image sensor can be shielded by appropriate filters blocking such excitation wavelengths from impinging on the second image sensor, and possibly the first image sensor if it is sensitive to that wavelength as well. The second light source can then be tuned or chosen to emit light in a wavelength range that can be mostly outside of those filter bands. The second light source can in this case be chosen with a power setting suitable to provide background lighting, but less than would be needed for fluorescence excitation.

If in an embodiment at least one of the first filter and the second filter can be arranged to be moved reversibly into and out of a beam path for the first sensor and second sensor, respectively, it can be possible to provide background images without restriction to the wavelength range of the respective light sources. For example, it would be possible to use a far red or near infrared fluorescence excitation light source such as a laser diode at a low power setting for background illumination when the respective filter has been removed from the optical path to the second image sensor. This means that in an embodiment, in the first lighting mode, the controller can be configured to activate the third light source as a second light source, such as at a low power setting, thus providing background lighting in the far red or near infrared spectrum. This can be further facilitated if in embodiments, the imaging unit has at least one first filter but no second filter, or, alternatively or additionally, a second filter can be moved out of the light path for the second sensor.

The system can be configured to provide far read and/or near infrared background lighting in either or both of the above-described configurations using a separate second light source or using a third, i.e., fluorescence excitation light source, as second light source.

In embodiments, the imaging unit can comprise at least two interchangeable camera units, a first camera unit having a filter or filters configured and arranged for the first lighting mode and a second camera unit having a filter or filters configured and arranged for the second lighting mode.

In some embodiments, the imaging unit can be a video endoscope having its own imaging optics and image sensors.

In alternative embodiments, the imaging unit can comprise one or more camera heads comprising the image sensors, and exchangeable optical devices, such as at least one of telescopes for endoscopic procedures, shortened telescopes for open surgery imaging and a fluorescence imaging adapter. In the case of one camera head, it can comprise switchable filters internally or externally for different lighting modes, or several different camera heads may be equipped with different filters for different lighting modes.

The fluorescence excitation light sources can be laser sources such as laser diodes, narrow-band LED sources or one or more Xenon light sources with filters, the light sources and/or filters can be tuned to excite pre-specified fluorescent dyes.

The medical multi-dye fluorescence imaging system can comprise a light source unit comprising one or more of the several light sources. In further embodiments, at least one of the second light source and the fourth light source may be located in a light source unit, in a camera head or in a fluorescence imaging adapter.

In embodiments, at least one of the at least one first filter and the at least one second filter can be a single, double or triple notch filter. Notch filters are filters filtering out narrow bands of the electromagnetic spectrum. These can be manufactured to predefined specifications, such as the frequencies and bandwidths of the pre-specified fluorescence excitation wavelengths, with single, double and triple notch filters having one, two or three, respectively, such filter bands simultaneously.

In an embodiment, at least one filter can be located in at least one of a camera head and an exchangeable optical device.

Such objective can also be solved by a method of medical multi-dye fluorescence imaging, such as using a previously described system, wherein in a first lighting mode for a first predetermined dye fluorescing in the visible spectrum, a first narrow band fluorescence excitation light can be generated in the visible spectrum and a second narrow band fluorescence excitation light can be generated in the far red or near infrared spectrum, fluorescent image data are taken with a first image sensor sensitive in the visible spectrum and background image data are taken with a second image sensor sensitive in the far red or near infrared spectrum, wherein the visible spectrum fluorescent image data are overlaid over the far red or near infrared background image data.

The method embodies the same features, characteristics and advantages as the afore-described system.

In embodiments, in a second lighting mode for a second predetermined dye fluorescing in the far red and/or near infrared spectrum, white illumination light can be generated as well as a second narrow band fluorescence excitation light in the far red or near infrared spectrum, background image data can be taken with a first image sensor sensitive in the visible spectrum and fluorescent image data can be taken with a second image sensor sensitive in the far red or near infrared spectrum, wherein the far red or near infrared spectrum fluorescent image data can be overlaid over the visible spectrum background image data.

In a further embodiment, in the first lighting mode, light having the wavelength of the first fluorescence excitation light can be filtered out from light impinging on the first image sensor, whereas light having the wavelength of the second fluorescence excitation light can be let through onto the second image sensor.

In a further embodiment, in the second lighting mode, light having the wavelength of the second fluorescence excitation light can be filtered out from light impinging on the second image sensor.

In another embodiment, in the first lighting mode, light from the second light source can be generated in a wavelength range lying at least partially outside fluorescence excitation wavelength bands being filtered out from impinging on the second image sensor.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

Figure 1:
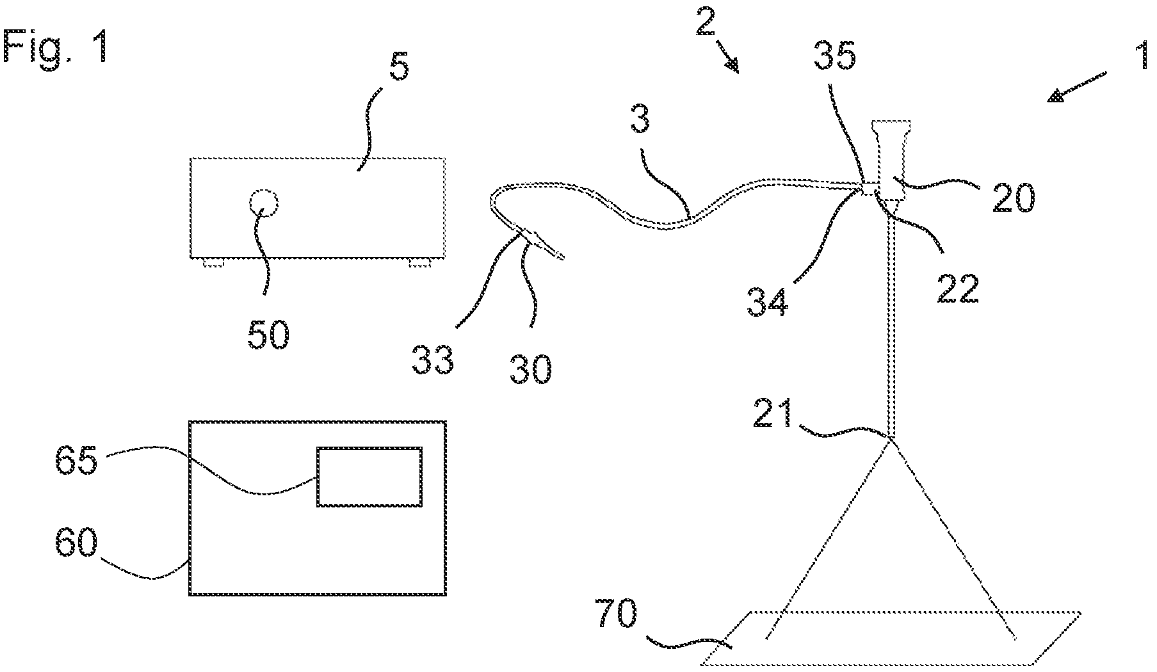
Figure 2:
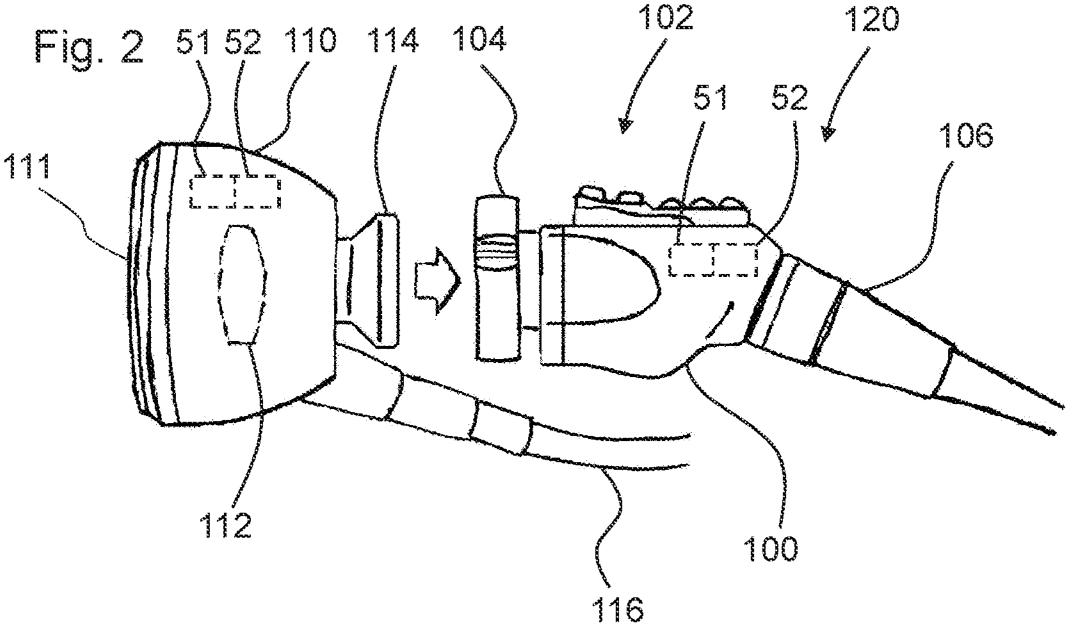
Figure 3:
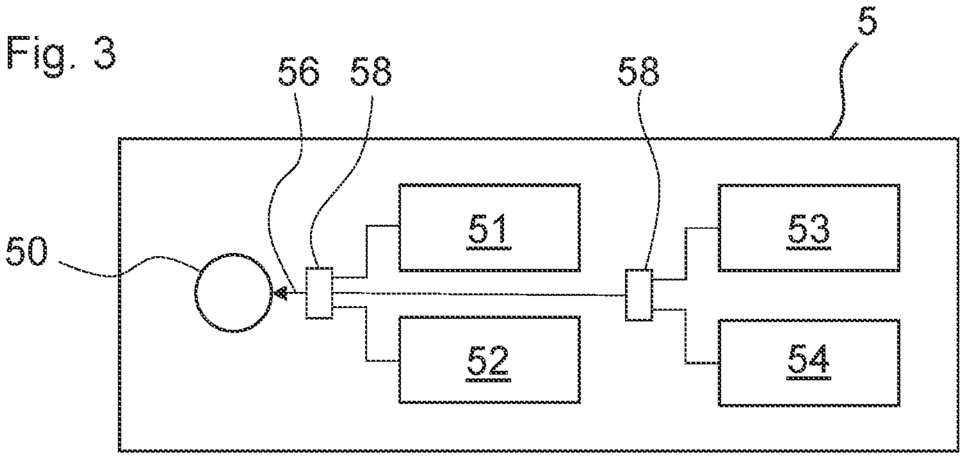
Figure 4:
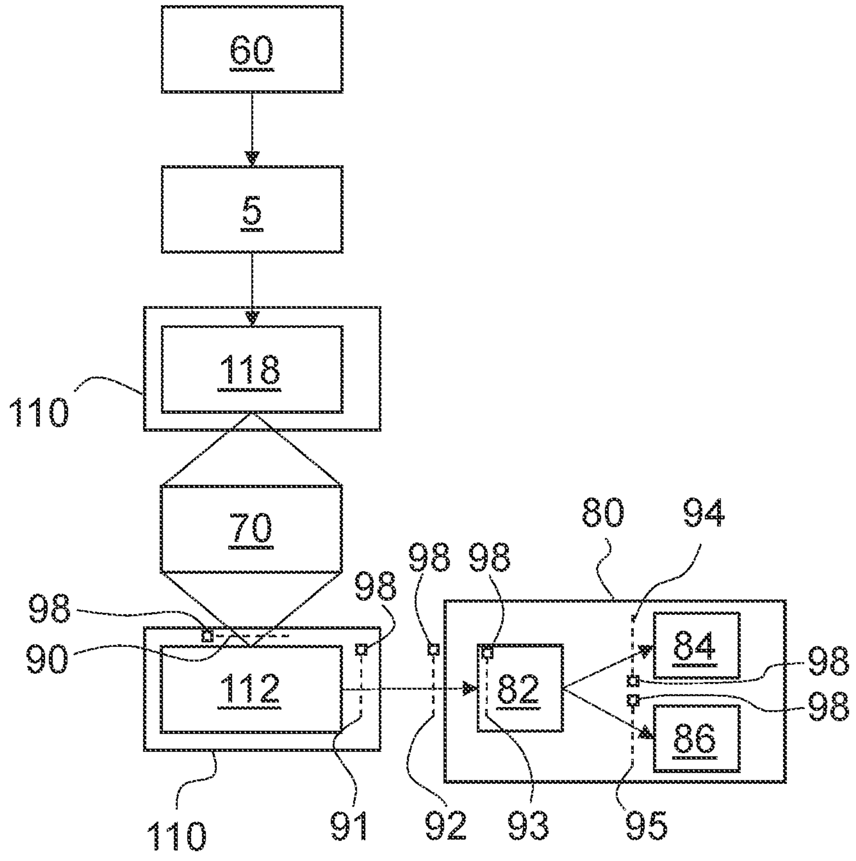

FIG. 1 illustrates a schematic simplified representation of an exoscope system comprising a light source and an exoscope with a light guide cable, FIG. 2 illustrates a schematic simplified representation of a camera head with a fluorescence imaging adapter, FIG. 3 illustrates a schematic representation of an embodiment of a light source unit of a system, and FIG. 4 illustrates a schematic of the illumination light path from the light source to the image sensors.

In the drawings, the same or similar types of elements or respectively corresponding parts are provided with the same reference numbers in order to prevent the item from needing to be reintroduced.

DETAILED DESCRIPTION

FIG. 1 shows a schematically simplified representation of an exoscope system used for open surgeries as a first example of a medical imaging system 1. The exoscope system 1 comprises an illumination light source unit 5 and an exoscope 2 with a light guide cable 3. The light guide cable 3 may be part of the exoscope 2 or separate to the exoscope 2. The exoscope 2 is configured to image an operating area 70 with an optical imaging unit (e.g., image sensor) not shown in FIG. 1. In order to illuminate the operating area 70 when observing it, the exoscope 2 further comprises illumination optics configured to guide light from the illumination light source unit 5 to an exoscope tip 21 of the exoscope 2. To this end, the light source unit 5, which is further described with reference to FIG. 3, comprises a light source port 50 configured to receive a light source connector 30 arranged at a first end 33 of the light guide cable 3. The second end 34 of the light guide cable 3 is connected to an exoscope body 20 of the exoscope 2. In the exemplary embodiment shown in FIG. 1, this is done with an exoscope connector 35 of the light guide cable 3 and a light guide cable connector 22 of the exoscope body 20. With these connectors 22, 35, the light guide cable 3 is detachable from the exoscope body 20. According to a different embodiment not shown in FIG. 1, the exoscope body 20 and the light guide cable 3 form a single unit and are not detachable from each other.

Inside the light guide cable 3 and the exoscope body 20, illumination light is guided through fiber bundles.

FIG. 1 also schematically displays a controller 60 comprising hardware set up to control the operation of the exoscope 2. Controller 60 can be configured as dedicated hardware circuits or a hardware processor executing a series of software instructions. The controller 60 can be set up to receive video signals from the exoscope 2, which may either be connected to a camera head connected to the exoscope, e.g., such as the one shown in FIG. 2, or have its own image sensor or sensors. The video signals are processed in an image processor 65, which may be integral with controller 60, a subunit of controller 60, or be external to and separate from the controller 60. Processor 65 can be configured as dedicated hardware circuits or a hardware processor executing a series of software instructions.

FIG. 2 illustrates a schematic representation of another medical imaging device, namely a combination of a camera head 100 and a fluorescence imaging adapter 110 as part of a second exemplary embodiment of a medical multi-dye fluorescence imaging system 120, which in addition may comprise a controller 60, such as a video controller, and light source unit 5 as displayed in FIG. 1. The camera head 100 is configured for white light imaging as well as fluorescence imaging. It is handheld and has control buttons 102 on the top of its housing, an adapter 104 for attachment of various optics systems at its front surface and a connecting cable 106 for power and signal transmission leading to a central controller such as the one shown in FIG. 1. Since the camera head 100 is configured to receive telescope type endoscopes with eyepieces (ocular cones), its adapter 104 may be configured to receive such eyepieces. The imaging optics of the camera head 100 is configured to have its focus at a location where the typically attached endoscopes project a virtual image to be viewed with the naked eye through the eyepiece. The eyepieces of endoscopes are usually adjusted so that the virtual image is about one meter in front of the eyepiece (−1 diopter). The exit pupil of the endoscopes is configured to approximately match the entrance pupil of the camera head and is located about 7 mm behind the edge of the eyepiece funnel, which is typically inside adapter 104 in the attached state.

The fluorescence imaging adapter 110 differs from endoscopes and exoscopes in that it does not have imaging optics, i.e., it does not produce a virtual image. Instead, it provides a head lens or attachment lens in the form of a head lens system 112 having one or more individual lenses whose function it is to change the properties of the imaging optics of camera head 100, rendering the camera head 100 capable of viewing the operating field. This can be done, e.g., by decreasing the focal length of the camera head 100 and thereby enlarging its field of view. Although the head lens system 112 itself does not provide a virtual image to be viewed with the naked eye, the fluorescence imaging adapter has a standardized ocular cone 114 on its rear side for the purpose of connecting to the adapter 104 of camera head 100.

Furthermore, the fluorescence imaging adapter 110 is equipped with a light guide cable 116 leading towards its front surface 111. The other end of the light guide cable 116 may be connected to an illumination light source unit 5 as shown in FIG. 1.

Whereas it would be typically envisioned that a first light source 51 generating fluorescence excitation light in the visible spectrum and/or a second light source 52 generating background illumination in the far red and/or near infrared spectrum would be co-located in the light source unit 5 shown in FIG. 1, alternative locations for one or both of first light source 51 and second light source 52 may also be inside the camera head 100 and/or the fluorescence imaging adapter 110, as shown with the dashed-line contoured boxes shown in FIG. 2. For example, only one of first and second light sources 51, 52 may be located either in the camera head 100 or the fluorescence imaging adapter 110, the other light source being located in light source unit 5. Alternatively, both of first and second light sources 51, 52 may be co-located in either the camera head 100 or the fluorescence imaging adapter 110. Finally, one of the first and second light sources 51, 52 may be located in the camera head 100, the other one in the fluorescence imaging adapter 110. With these options, it is possible to upgrade existing systems without having to alter the light source unit 5.

FIG. 3 schematically shows a light source unit 5 to be used with a system as shown, for example, in the embodiments of FIGS. 1 and 2, in more detail. In the present example, the light source unit 5 comprises four light sources 51, 52, 53, 54 that feed light generated by any of the light sources 51, 52, 53, 54 to the light source port 50 by a light guide 56, which may consist of light guiding fibers, light guiding optics or light guides made from transparent material, such as glass or transparent plastic material, such as an acrylic glass (e.g., Plexiglas®) or other commonly known means.

Light from the different light sources 51, 52, 53, 54 may be combined into the light guide 56 by means of one or several light guide couplers 58, such as optical fiber couplers, or transparent light guides in a shape that narrows from an input side accommodating several input light guides to a smaller output side accommodating only one output light guide, combining the light output of several light guides such as optical fibers using the principle of total internal reflection.

The light sources, which are controlled by a controller, such as controller 60 depicted in FIG. 1, are of different types. A first light source 51 may be a narrow-band fluorescence excitation light source in the visible spectrum such as a laser diode, an LED light source or a Xenon lamp with appropriate filters. The first light source 51 may generate fluorescence excitation light for example at or around 488 nm. The exact wavelengths of the different fluorescent excitation lights are to be chosen with respect to efficiently exciting the fluorescence dyes for which the system is laid out.

A third light source 53 may be another fluorescence excitation light source. This may be a narrowband light source, such as an LED or laser source, for example a laser diode, configured to generate fluorescence excitation light in the far red or infrared region of the optical spectrum. There may be several third light sources 53. For example one third light source may be tuned in the far red region for a first fluorescence dye, for example at or around 680 nm, whereas another third light source 53 may be tuned in the near infrared region, for example at or around 780 nm, for a second fluorescent dye having a fluorescence spectrum that is shifted further into the infrared region than the first fluorescence dye.

A second light source 52 provides background illumination in the far red and/or near infrared spectrum. It may be a dedicated source, such as an LED light source generating light outside the filter windows used to filter out fluorescence excitation light before reaching the second image sensor and, if applicable, the first image sensor, if the latter has residual sensitivity to the wavelength of the far red fluorescence excitation light. Alternatively, a third light source 53 may be used at a low power setting as or instead of second light source 52 to produce far read or near infrared background illumination provided that it is assured that the optical setup does not include a filter for the wavelength produced by the third light source 53. This may include an exchangeable setup or a removable filter.

A fourth light source 54 is a white illumination light source. The fourth light source 54 generates visible light across most or all of the visible spectrum in order to provide full white background illumination. Alternatively, white illumination fourth light source 54 may also comprise subunits generating different color lighting, for example red, green and blue that, when mixed together, produce white illumination. Such subunits may comprise differently colored LEDs or differently tuned lasers.

In FIG. 4, the illumination light path from the light source unit 5 to image sensors 84, 86 of an imaging unit 80 is illustrated schematically. Depending on the lighting mode chosen by a doctor performing a surgical or diagnostic procedure involving fluorescence imaging on the basis of fluorescence imaging, the controller 60 directs the light source unit 5, a nonlimiting example of which has been described in FIG. 3, to generate illumination lighting and fluorescence excitation lighting. In a first lighting mode, the controller 60 may control the light source unit 5 to activate a first light source 51 and a second light source 52 in order to generate narrowband lighting in the far red and/or near infrared spectrum as well as in the visible spectrum, wherein the lighting in the far red and/or near infrared spectrum serve for background illumination, providing a monochrome background image, whereas the fluorescence excitation light in the visible range is used to excite the fluorescent dye that is active in the visible part of the optical spectrum.

In a second lighting mode, controller 60 directs the light source unit 5 to generate white illumination lighting using fourth light source 54 for a full-color background image as well as far red or near infrared fluorescence excitation lighting for the fluorescence imaging overlay using light source 53, dependent on the specific fluorescence dye chosen for the respective procedure and application.

The light generated by at least two of the light sources of light source unit 5 is coupled out of light source unit 5 and into the device that serves to illuminate an operating area 70, which may be an external area such as shown in FIG. 1 or inside the body in an endoscopic procedure. In the example shown in FIG. 4, the device is the fluorescence imaging adapter 110 as shown in FIG. 2 and having illumination lighting means 118, for example the polished ends of light guiding fibers. The illumination light is reflected from the operating area 70 back to a head lens system 112 of fluorescence imaging adapter 110, carrying all the visual information of the background image as well as from any fluorescent de-excitation taking place inside the illuminated field of view.

The head lens system 112 relays the light entering the head lens system 112 towards imaging unit 80, which may be the camera head 100 shown in FIG. 2. Alternatively, the imaging unit 80 may include all of the optical elements involved, making superfluous a separate optics unit as that in the fluorescence imaging adapter 110.

Inside the imaging units 80, the incoming light first impinges on a splitter 82, which may be a beam splitter, beam divider or prism, and which is configured to separate the incoming light into two different light paths, while simultaneously providing a wavelength selection functionality that passes light having wavelengths that are smaller than a cut off wavelength, for example 700 nm, to a first image sensor 84 and light having wavelengths bigger than the cut off wavelength to second image sensor or 86. First image sensor 84 is sensitive to visible light, whereas second image sensor 86 is sensitive to light in the far red and/or near infrared spectrum. In practice, the sensitive wavelength ranges of the two image sensors 84, 86 may overlap somewhat.

In the above-mentioned first lighting mode, second image sensor 86 provides a monochrome background image, whereas first image sensor 84 provides fluorescent image signals in the visible spectrum. In the second lighting mode, the situation is reversed and first image sensor 84 provides full color background imaging, whereas second image sensor 86 provides far red and/or near infrared fluorescence imaging for the overlay.

In fluorescence imaging, it is important that the fluorescence excitation lighting is barred from reaching the respective image sensor that is responsible for providing the fluorescence overlay image. Such reflected illumination light would drown out any fluorescence signal that is generated at larger wavelengths, which is much weaker. For this purpose, a filter is usually used, for example a notch filter, that filters out light within a very narrow wavelength range or several narrow wavelength ranges that is or are centered on the wavelength or wavelengths that are or can be generated by the fluorescence light sources 51, 53. Such filters may be located at different locations along the lighting path.

A first such location is the entrance to the head lens system 112 of fluorescence imaging adapter 110, where a filter 90 may be located. The filter 90 may be external or internal to the fluorescence imaging adapter 110. For the first lighting mode described above, filter 90 has a notch filter whose range is centered around the visible spectrum wavelengths generated by first light source 51. However, filter 90 does not have another notch filter range in the far red or near infrared spectral range for the wavelengths generated by second light source 52, since its light is used for background illumination, not fluorescence, and must reach second image sensor 86. For the second lighting mode, filter 90 is equipped to filter out far red and/or near infrared fluorescence excitation lighting generated by third light source 53. It may, but need not, also be equipped with a filter characteristic for filtering out visible spectrum fluorescence excitation lighting which may be generated by or contained within the emission spectrum of fourth light source 54.

Since the filter characteristic changes between the first and second lighting modes, two different filters 90 may have to be used, such as if second light source 52 is itself a fluorescence excitation light source such as third light source 53. This can be achieved by various means. For example, there may be two different filters providing the respective filter characteristics for the first and second lighting modes that can be exchanged for one another by affixing their respective filter from the outside to the head lens system 112 of fluorescence imaging adapter 110. Alternatively, filter 90 may be a switchable filter included in fluorescence imaging adapter 110, where the filter having the appropriate filter characteristics for the chosen lighting mode is switched or rotated into the light path. Finally, there may be two or more fluorescence imaging adapters 110 that each have the filter 90 with the appropriate filter characteristics for the chosen lighting mode.

In the same way, alternatively, such filters 91, 92, 93 may be located at different locations, such as at the exit of head lens system 112, between fluorescence imaging adapter 110 and imaging unit 80 or at the entrance to splitter 82 inside imaging unit 80. In each of these locations, filters 91, 92 or 93 are either exchangeable or, if applicable, there may be several fluorescence imaging adapters 110 with different filters 94 for different lighting modes.

It is also possible to use filters 90, 91, 92, 93 at different locations for providing different filter characteristics. For example filter 90 inside the fluorescence imaging adapter 110 may provide a notch filter for the visible light fluorescence excitation lighting, whereas filter 91 may provide a notch filter for the far red and/or near infrared fluorescence excitation light wavelengths. Both filters may be switched or rotated into and out of the optical path in order to switch between lighting modes, or filter 90 may be fixed.

A final location for filters 94, 95 is between splitter 82 and first and second image sensors 84, 86, filter 94 being assigned to first image sensor 84 and filter 95 to second image sensor 86. At this location, filter 94 is provided with notch filter characteristics for the visible light fluorescence excitation lighting wavelength of first light source 51, whereas filter 95 is provided with notch filter characteristics for the far red and/or near infrared spectrum fluorescence excitation lighting wavelengths of third light source 53. In this case, too, one or more of filters 94 and 95 may be switchable or rotatable into and out of the impasse between splitter 82 and first and second image sensors 84, 86.

The switching or rotating of filters 90, 91, 92, 93, 94, 95 may be achieved by using a filter switch 98 such as a filter wheel with an axis of rotation aligned with a central optical axis of the optical path, or a switching mechanism that either pushes the filter into and out of the beam path or rotates the filter around a hinge, or rotates a filter assembly around an axis of rotation that is perpendicular to the central optical axis of the optical path. Switchable and rotatable filter assemblies are known in the art of endoscopes.

Alternatively, the system may comprise several imaging units 80 or, respectively, camera heads 100, that may be equipped with different sets of filters 93, 94 and/or 95 for different lighting modes.

Instead of the camera head 100 and fluorescence imaging adapter 110, the same principle as shown in FIG. 4 also applies in other medical multi-dye fluorescence imaging systems that employ video endoscopes or combinations of camera heads with other optical devices such as telescopes, for example, or other instruments that may in their combination constitute a versatile system.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

1 medical multi-dye fluorescence imaging system
2 exoscope
3 light guide cable
5 light source unit
20 exoscope body
21 exoscope tip
22 light guide cable connector
30 light source connector
33 first end
34 second end
35 medical imaging device connector
50 light source port
51 first light source
52 second light source
53 third light source
54 fourth light source
56 light guide
58 light guide coupler
60 controller
65 image processor
70 operating area

80 imaging unit
82 splitter
84 first image sensor
86 second image sensor
90-95 filter
98 filter switch
100 camera head
102 control buttons
104 adapter for attachment devices
106 connecting cable
110 fluorescence imaging adapter
111 front surface
112 head lens system
114 ocular cone
116 light guide cable
118 illumination lighting means
120 medical multi-dye fluorescence imaging system

What is claimed is:

1. A medical multi-dye fluorescence imaging system comprising:

a controller comprising hardware, a plurality of light sources controlled by the controller, at least one imaging unit comprising a first image sensor sensitive in a visible light spectrum and a second image sensor sensitive in one or more of a far red and a near infrared light spectrum, the controller being configured to:

receive first image data from the first image sensor and second image data from the second image sensor and combine the first and second image data into composite images in which fluorescent images are overlayed over background images, control the plurality of light sources according to a first lighting mode for at least one first predetermined fluorescent dye fluorescing in the visible light spectrum, the first lighting mode comprising:

activating a first light source of the plurality of light sources configured to produce excitation light for the at least one first predetermined dye in the visible light spectrum, activate a second light source of the plurality of light sources configured to produce light in one of the far red and the near infrared light spectrum, and overlay the first image data from the first image sensor over the second image data from the second image sensor;

wherein the second light source is operated with a power setting suitable to provide background lighting, but less than would be needed for fluorescence excitation.

2. The medical multi-dye fluorescence imaging system according to claim 1, wherein the controller is further configured to control the plurality of light sources according to a second lighting mode for at least one second predetermined fluorescent dye fluorescing in one of the far red and the near infrared light spectrum, the second lighting mode comprising:

activating a third light source of the plurality of light sources configured to produce excitation light for the at least one second predetermined dye in one of the far red and the near infrared light spectrum, activating a fourth light source of the plurality of light sources configured to produce white illumination light, and overlaying the second image data from the second image sensor over the first image data from the first image sensor.

3. The medical multi-dye fluorescence imaging system according to claim 2, wherein the at least one imaging unit comprising at least one of:

at least one first filter configured and located to prevent excitation light from the first light source from reaching the first image sensor; and at least one second filter configured and located to prevent excitation light from the third light source from reaching the second image sensor.

4. The medical multi-dye fluorescence imaging system according to claim 3, wherein the second light source being configured to emit light in a spectrum lying at least partially outside of any frequencies filtered out by the at least one second filter.

5. The medical multi-dye fluorescence imaging system according to claim 3, wherein at least one of the at least one first filter and the at least one second filter being movable into and out of a beam path for the first image sensor and the second image sensor, respectively.

6. The medical multi-dye fluorescence imaging system according to claim 3, wherein in the first lighting mode, the controller being configured to activate the third light source as the second light source.

7. The medical multi-dye fluorescence imaging system according to claim 6, wherein at least one of:

the at least one imaging unit having the at least one first filter and not having the at least one second filter; and/or the at least one second filter is movable out of the light path for the second image sensor.

8. The medical multi-dye fluorescence imaging system according to claim 3, wherein at least one of the at least one first filter and/or the at least one second filter is one of a single, double or triple notch filter.

9. The medical multi-dye fluorescence imaging system according to claim 3, wherein at least one of the first and second filters is located in at least one of a camera head and an exchangeable optical device.

10. The medical multi-dye fluorescence imaging system according to claim 2, wherein the at least one imaging unit comprising at least two interchangeable camera units, the at least two interchangeable camera units comprising a first camera unit having at least one filter configured and arranged for the first lighting mode and a second camera unit having at least one filter configured and arranged for the second lighting mode.

11. The medical multi-dye fluorescence imaging system according to claim 2, wherein at least one of the second light source and the fourth light source is located in one of a light source unit, a camera head or a fluorescence imaging adapter.

12. The medical multi-dye fluorescence imaging system according to claim 1, wherein the at least one imaging unit is a video endoscope having imaging optics and the first and second image sensors.

13. The medical multi-dye fluorescence imaging system according to claim 1, wherein the at least one imaging unit comprises one or more camera heads comprising the first and second image sensors, and exchangeable optical devices.

14. The medical multi-dye fluorescence imaging system according to claim 13, wherein the exchangeable optical devices comprise at least one of telescopes for endoscopic procedures, shortened telescopes for open surgery imaging and a fluorescence imaging adapter.

15. The medical multi-dye fluorescence imaging system according to claim 1, wherein the first light source for producing excitation light comprises one of a laser source, a narrow-band light-emitting diode (LED) source or one or more Xenon light sources with filters.

16. The medical multi-dye fluorescence imaging system according to claim 1, wherein one or more of the first light source and/or filters being tuned to excite pre-specified fluorescent dyes.

17. The medical multi-dye fluorescence imaging system according to claim 1, further comprising a light source unit comprising the plurality of light sources.

18. A method of medical multi-dye fluorescence imaging comprising:

receiving first image data from a first image sensor and second image data from a second image sensor and combining the first and second image data into composite images in which fluorescent images are overlayed over background images, controlling a plurality of light sources according to a first lighting mode for at least one first predetermined fluorescent dye fluorescing in the visible light spectrum, the first lighting mode comprising:

activating a first light source of the plurality of light sources configured to produce excitation light for the at least one first predetermined dye in the visible light spectrum, activating a second light source of the plurality of light sources configured to produce light in one of a far red and a near infrared light spectrum, and overlaying the first image data from the first image sensor over the second image data from the second image sensor;

wherein the second light source is operated with a power setting suitable to provide background lighting, but less than would be needed for fluorescence excitation.

19. The method according to claim 18, wherein in a second lighting mode for a second predetermined dye fluorescing in the far red and/or the near infrared spectrum, the method further comprising:

generating white illumination light and a second narrow band fluorescence excitation light in the far red or the near infrared spectrum, taking background image data with the first image sensor sensitive in the visible spectrum and taking fluorescent image data with the second image sensor sensitive in the far red or the near infrared spectrum, and wherein the far red or the near infrared spectrum fluorescent image data are overlaid over the visible spectrum background image data.

20. The method according to claim 19, wherein in the second lighting mode, the method comprising filtering light having the wavelength of the second narrow band fluorescence excitation light out from light impinging on the second image sensor.

21. The method according to claim 20, wherein in the first lighting mode, the method comprising generating light from the second light source in a wavelength range lying at least partially outside second fluorescence excitation wavelength bands being filtered out from impinging on the second image sensor.

22. The method according to claim 18, wherein in the first lighting mode, the method comprising filtering light having the wavelength of the first fluorescence excitation light from the first light source out from light impinging on the first image sensor, and letting through light having the wavelength of a second fluorescence excitation light onto the second image sensor.

* * * * *